(12) United States Patent
Christensen et al.

(10) Patent No.: US 11,723,520 B2
(45) Date of Patent: Aug. 15, 2023

(54) ARTICULATION ACTIVATION WIRE STRESS RELIEF FOR AN ULTRASOUND IMAGING PROBE

(71) Applicant: B-K Medical Aps, Herlev (DK)

(72) Inventors: Bjarne Lasse Christensen, Koege (DK); Niels-Christian LL Sasady, Frederiksberg (DK)

(73) Assignee: B-K MEDICAL APS, Herlev (DK)

( * ) Notice: Subject to any disclaimer, the term of this patent is extended or adjusted under 35 U.S.C. 154(b) by 139 days.

(21) Appl. No.: 17/157,081

(22) Filed: Jan. 25, 2021

(65) Prior Publication Data
US 2021/0137353 A1 May 13, 2021

Related U.S. Application Data

(62) Division of application No. 15/543,651, filed as application No. PCT/IB2015/050348 on Jan. 16, 2015, now Pat. No. 10,939,808.

(51) Int. Cl.
*A61B 1/005* (2006.01)
*A61B 8/00* (2006.01)
(Continued)

(52) U.S. Cl.
CPC ............ *A61B 1/0052* (2013.01); *A61B 1/008* (2013.01); *A61B 1/0057* (2013.01); *A61B 8/12* (2013.01);
(Continued)

(58) Field of Classification Search
CPC . A61B 1/00133; A61B 1/0052; A61B 1/0057; A61B 1/008
See application file for complete search history.

(56) References Cited

U.S. PATENT DOCUMENTS 4,207,873 A * 6/1980 Kruy .................... A61B 1/0052
600/146
4,294,233 A * 10/1981 Takahashi ............ A61B 1/0052
600/149
(Continued)

OTHER PUBLICATIONS

International Search Report for PCT/IB2015/050348 published as WO2016/113600 A1 dated Jul. 21, 2016.
(Continued)

*Primary Examiner* — Aaron B Fairchild
(74) *Attorney, Agent, or Firm* — Daugherty & Del Zoppo, III Co. LPA

(57) ABSTRACT

A probe includes an articulating member with at least two vertebrae elements sequentially arranged along a long axis of the elongate ultrasound imaging probe. The articulating member includes pivots located between the at least two vertebrae elements. The pivots are disposed off-center relative to the at least two vertebrae elements. The pivots are spatially oriented to provide a pivot point for a different articulation direction of a vertebra element. The probe further includes a plurality of guides, including at least one guide for each of the respective different pivot directions. The probe further includes an actuator with a set of controls, each control configured to actuate a different pair of the plurality of guides for controlling opposing articulation directions, wherein the actuator reduces stress induced on at least one of a pushed guide or a non-activated guide, wherein the stress is induced in response to the actuator pulling a guide.

9 Claims, 7 Drawing Sheets

(51) Int. Cl.
    *A61B 8/12*        (2006.01)
    *A61B 1/008*      (2006.01)
    *A61B 1/00*       (2006.01)
    *A61B 1/267*      (2006.01)

(52) U.S. Cl.
    CPC .......... *A61B 8/445* (2013.01); *A61B 1/00006* (2013.01); *A61B 1/00016* (2013.01); *A61B 1/00133* (2013.01); *A61B 1/267* (2013.01)

(56) References Cited

U.S. PATENT DOCUMENTS

| | | |
|---|---|---|
| 4,688,555 A | 8/1987 | Wardle |
| 5,413,107 A | 5/1995 | Oakley et al. |
| 8,808,169 B2 * | 8/2014 | Macnamara ........... A61B 1/005 600/149 |
| 2008/0139886 A1 | 6/2008 | Tatsuyama |
| 2012/0046522 A1 | 2/2012 | Naito |
| 2018/0000315 A1 | 1/2018 | Christensen et al. |

OTHER PUBLICATIONS

U.S. Appl. No. 15/543,651, filed Jul. 14, 2017, Confirmation No. 1601.

* cited by examiner

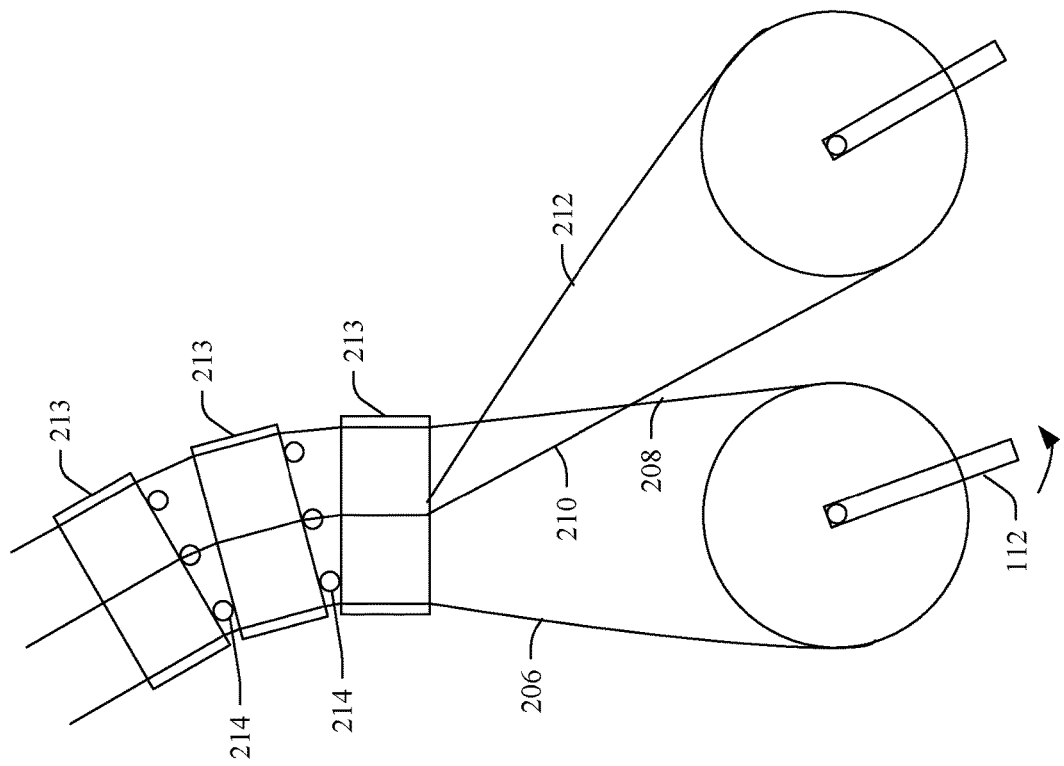
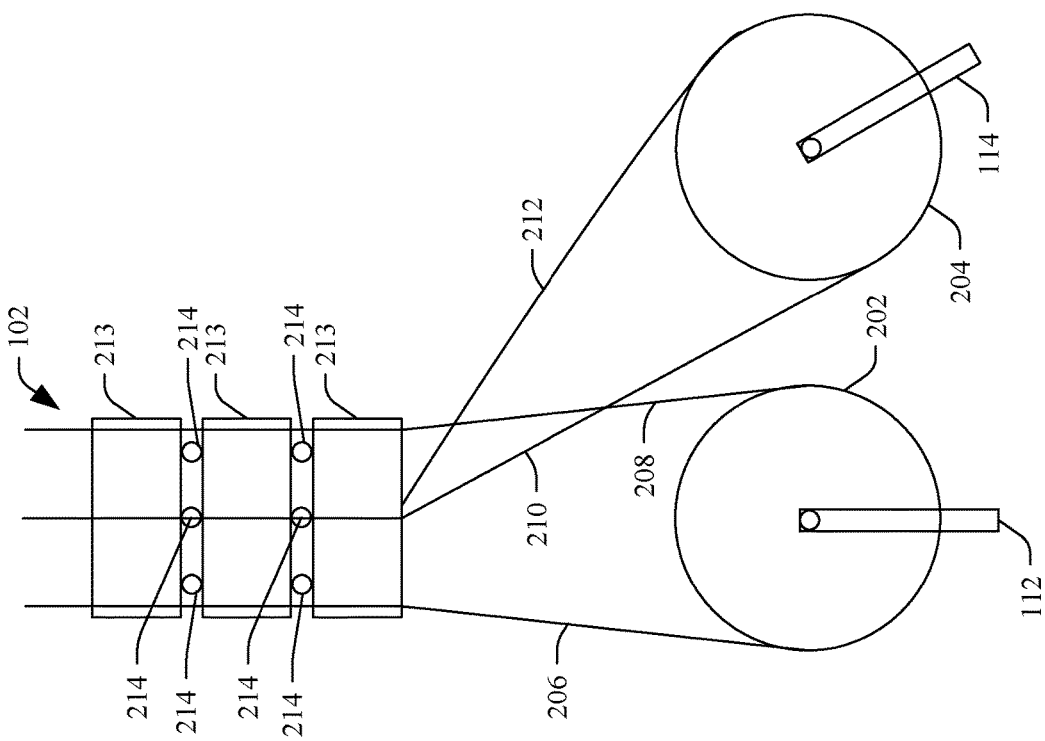

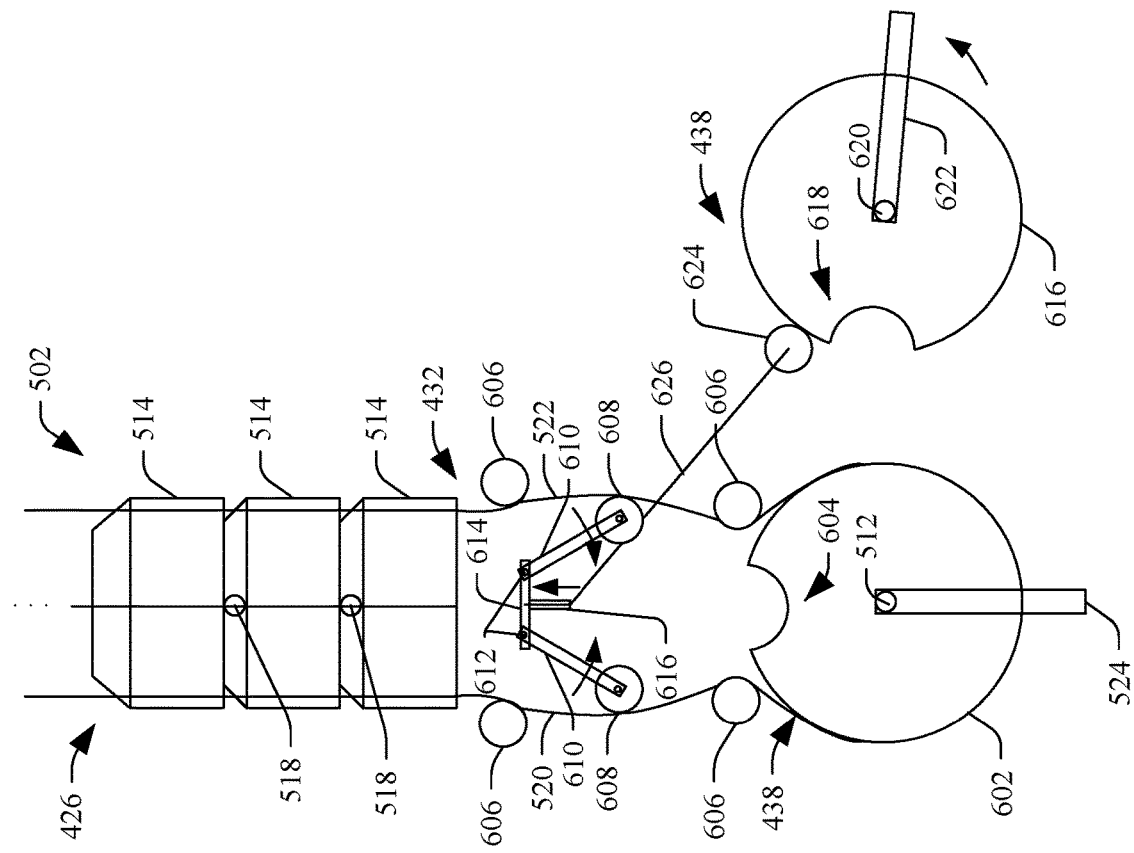
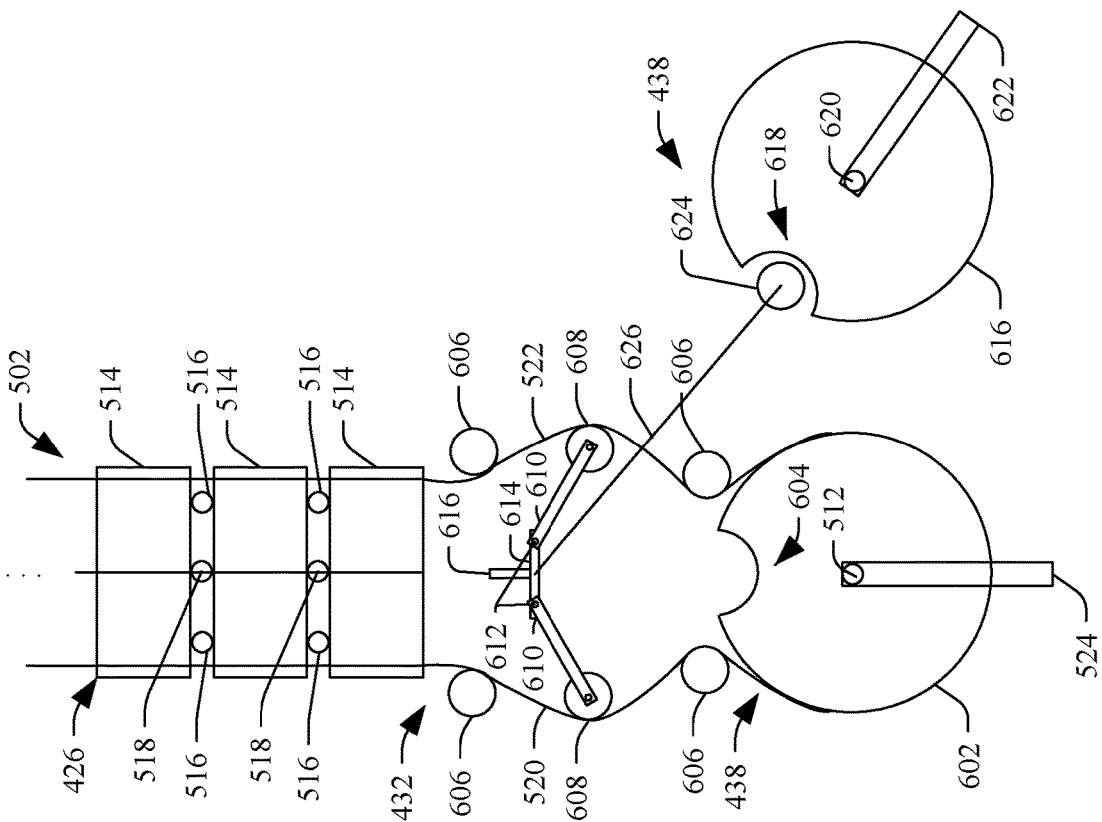

ARTICULATION ACTIVATION WIRE STRESS RELIEF FOR AN ULTRASOUND IMAGING PROBE

TECHNICAL FIELD

The following generally relates to ultrasound (US) imaging and more particularly to articulation activation wire stress relief for an ultrasound imaging probe.

BACKGROUND

There are at least two different types of ultrasound imaging probes—flexible and rigid. Flexible ultrasound probes include an articulating portion that is controllably articulated to move the end of the probe head and the transducer array through an angle of, e.g., up to 180° degrees in one to four planes. FIGS. 1A and 1B show an example of a flexible probe 100; namely, a laparoscopic transducer type 8666, which is a product of BK-Medical ApS, a company of Herlev, Denmark. In FIG. 1A, an articulating portion 102 is configured to articulate to an up position 104 or a down position 106. A lever 112 controls up/down articulation. In FIG. 1B, the articulating portion 102 is further configured to articulate to a left position 108 or a right position 110. A lever 114 controls left/right articulation. Generally, either the first lever 112 or the second lever 114 is employed during an examination, but not concurrently both of the levers 112 and 114.

FIG. 2A shows the lever 112 attached to a cam 202 and the lever 114 attached to a cam 204. A first wire 206 is connected between a first side of the cam 202 and a first side of the articulating portion 102, and a second wire 208 is connected between a second opposing side of the cam 202 and a second opposing side of the articulating portion 102. A third wire 210 is connected between a first side of the cam 204 and a third side of the articulating portion 102, and a fourth wire 212 is connected between a second side of the cam 204 and a fourth side of the articulating portion 102. The lever 112 rotates the cam 202, and the lever 114 rotates the cam 204. Rotating one of the cams 202 or 204 causes the corresponding wires to push on one side and pull on the opposing side of the articulating portion 102, which causes the articulating portion 102 to articulate. The articulating portion 102 includes a plurality of vertebrae 213 separated by pivots 214. Between neighboring vertebrae 213, a first pair of pivots 214 is for left/right articulation and a second pair of pivots 214 is for up/down articulation. The pivots 214 are located off center with respect to the articulating portion 102.

In FIG. 2B, the lever 112 is rotated counter-clockwise, which pulls on the wire 206 and pushes on the wire 208 resulting in left articulation. Since the pivots 214 are off center, the pull and push lengths of the wires 206 and 208 are not the same. That is, a push length is longer than a pull length. However, the cam 202 releases only a same length of wire, which is the pull length. As a consequence, a stress is induced in the pushed wire. Rotating the lever 112 clockwise, the lever 114 counter-clockwise, or the lever 114 clockwise likewise induces a stress in the pushed wire. FIGS. 3A and 3B show down and up articulation with the lever 114. Furthermore, both of the wires of the non-activated lever will be likewise stressed. This can be seen in FIG. 2B (wires 210 and 212) and FIGS. 3A and 3B (wires 206 and 208). One approach to mitigate these stresses are to include springs in the wires. Unfortunately, with such an approach, the springs introduce slack in the wires, causing a delay between the articulation expected by the user and the actual articulation.

SUMMARY

Aspects of the application address the above matters, and others.

In one aspect, an elongate ultrasound imaging probe includes an articulating member. The articulating member includes at least two vertebrae elements sequentially arranged along a long axis of the elongate ultrasound imaging probe. The articulating member further includes a plurality of pivots located between the at least two vertebrae elements. Each of the plurality of pivots is disposed off-center relative to the at least two vertebrae elements. Each of the plurality of pivots is spatially oriented to provide a pivot point for a different articulation direction of a set of different of articulation directions of a vertebra element of the plurality of vertebrae elements. The probe further includes a plurality of guides, including at least one guide for each of the respective different pivot directions. An actuator with a set of controls, each control configured to actuate a different pair of the plurality of guides for controlling opposing articulation directions, wherein the actuator reduces stress induced on at least one of a pushed guide or a non-activated guide, wherein the stress is induced in response to the actuator pulling a guide.

In another aspect, an elongate ultrasound imaging probe includes a flexor configured to flex a tip of the probe, where the tip of the probe houses a transducer array, a flexor control system configured to control the flexor to flex the tip in one of a plurality of different directions through pulling and pushing on guides affixed to the flexor, and a flexor actuator configured to actuate the flexor control system to selectively pull and push on the guides.

In another aspect, an ultrasound imaging system includes a probe and a console. The probe includes a probe head with a transducer array, a shaft, an articulating member disposed between the probe head and the shaft, an articulating member actuator configured to control the articulating member through guide wires, wherein the articulating member reduces stress in the guide wires through a structural elements that slack off at least one of a pushed guide wire or a non-activated guide wire in response to at least one pulled guide wire, and a console interface. The console includes ultrasound imaging components and a probe interface. The console and probe interfaces are complementary interfaces, providing an electrical communications path between the probe and the console.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIG. 2A illustrates example control of the articulation of the probe of FIGS. 1A and 2B;

FIG. 2B illustrates left articulation and stress induced on the pushed wire and the non-actuated wires of the probe of FIGS. 1A and 2B;

FIG. 6A illustrates another example of the articulation sub-system.

FIG. 6B illustrates the example articulation sub-system of FIG. 6A in use.

DETAILED DESCRIPTION

Figure 4:
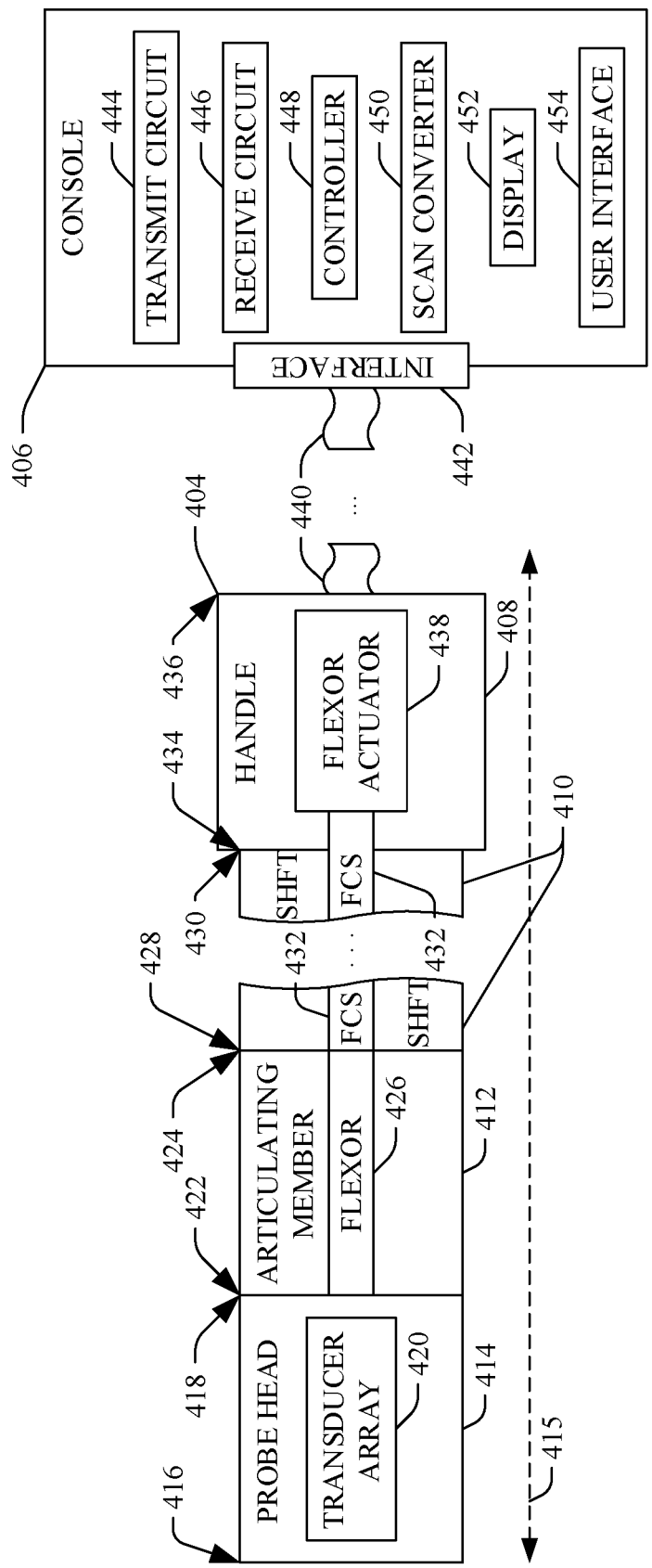
FIG. 4 schematically illustrates an example ultrasound imaging system with probe with an articulation sub-system.

FIG. 4 illustrates an imaging system 402 such as ultrasound imaging system. The imaging system 402 includes an elongate ultrasound probe 404 and a console 406. The elongate ultrasound probe 404 includes a handle 408, a shaft (SHFT) 410, an articulating member 412, and a probe head 414. The handle 408, the shaft 410, the articulating member 412 and the probe head 414 respectively are arranged with respect to each along a longitudinal axis 415 of the elongate ultrasound probe 404.

The probe head 414 includes a first end region 416 and a second end region 418. In the illustrated embodiment, the probe head 414 also includes a transducer array 420. In another embodiment, the probe head 414 can also include a biopsy region. The first end region 416 includes the end of the probe 404. The second end region 418 is affixed to the articulating member 412. The transducer array 420 includes a one or two dimensional array transducer elements. Suitable configurations include, but are not limited to, linear, curved (e.g., convex), and phased arrays. The transducer array 420 is configured to acquire data for A-mode, B-mode, etc. acquisitions, individually and in combination with color flow, Doppler flow, etc.

The articulating member 412 includes a first end region 422, a second end region 424 and a flexor 426. The first end region 416 is affixed to the second end region 418 of the probe head 414. The second end region 424 is affixed to the shaft 410. The flexor 426 extends along the longitudinal axis 415. The flexor 426 is configured to flex the articulating member 412 to various positions, e.g., in one to four planes through angles of up to ninety (90) degrees or more. Examples of suitable positions include up, down, left, right and/or other positions. As described in greater detail below, in one instance, the flexor includes a plurality of vertebrae with pivots there between.

The shaft 410 includes a first end region 428, a second end region 430, and at least a first portion of the flexor control system (FCS) 432. The first end region 428 is affixed to the second end region 424 of the articulating member 412. The second end region 430 is affixed to the handle 408. The flexor control system 426 extends along the longitudinal axis 415. The flexor control system 426 is configured to push and pull on the flexor 426 to flex the articulating member 412 for up/down and left/fight articulation. As described in greater detail below, in one instance, the flexor control system 432 includes a plurality of guides such as wires that pull and push on the vertebrae, pivoting them on the pivots.

Figure 1A:
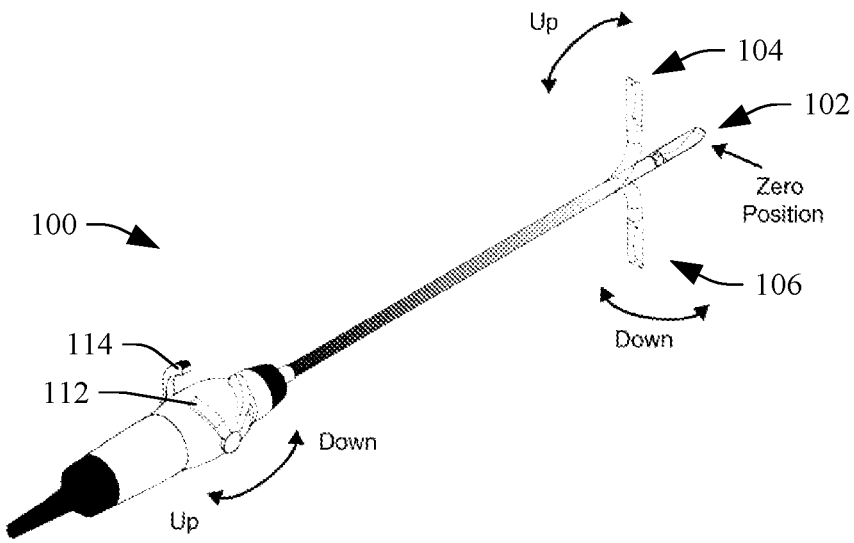
FIG. 1A illustrates up/down articulation of a probe head of a prior art ultrasound imaging probe.
Figure 1B:
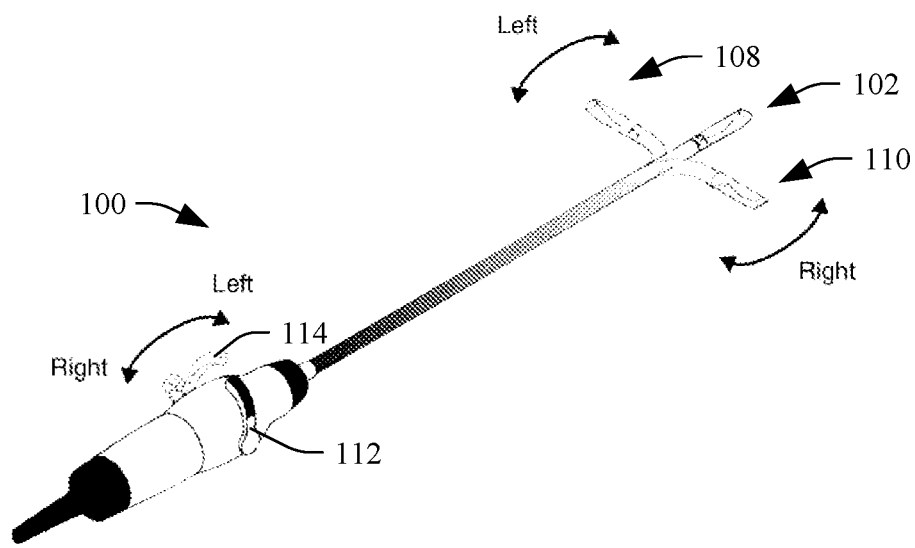
FIG. 1B illustrates left/right articulation of the probe head of the prior art ultrasound imaging probe of FIG. 1A.
Figure 3B:
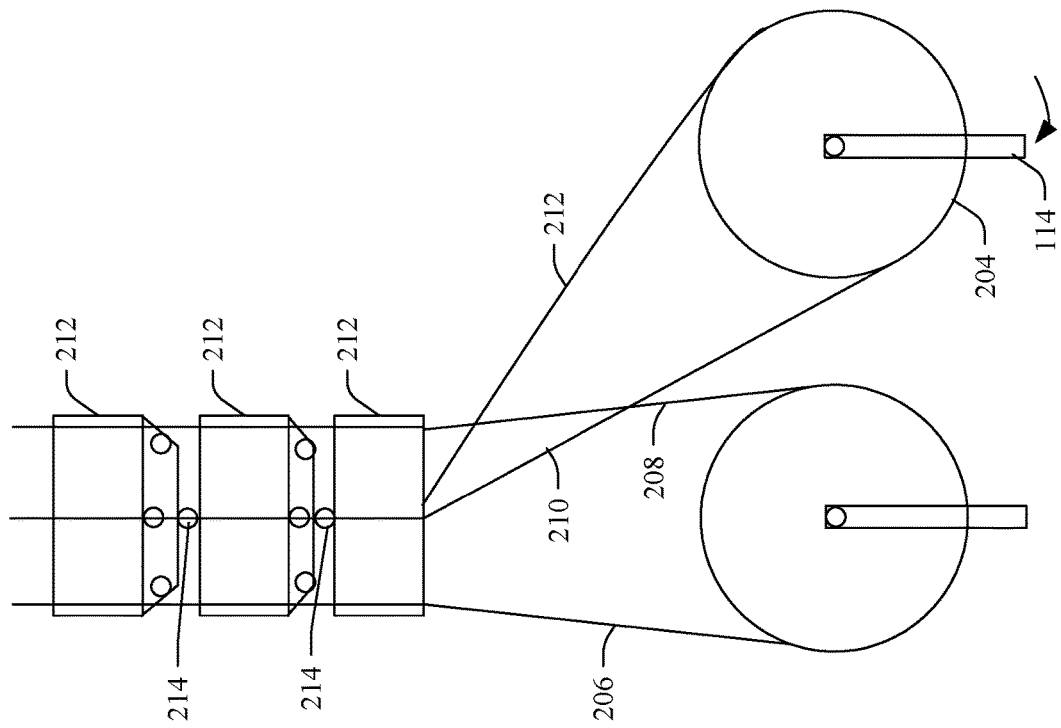
FIG. 3B illustrates up articulation and stress induced on the pushed wire and the non-actuated wires of the probe of FIGS. 1A and 2B.
Figure 3A:
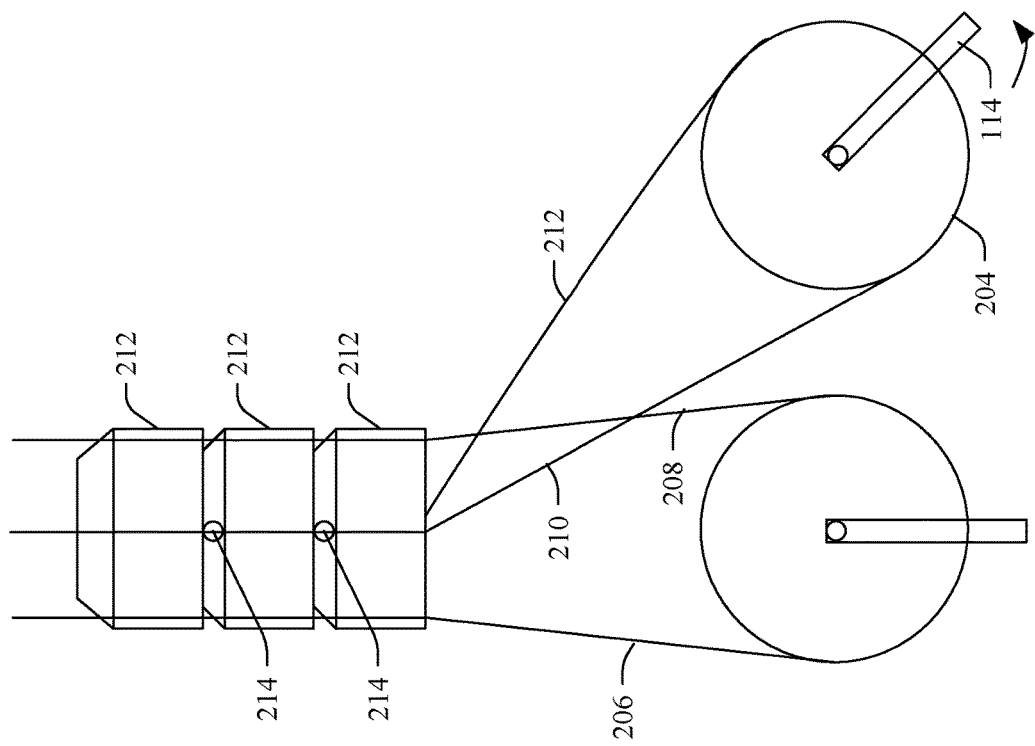
FIG. 3A illustrates down articulation and stress induced on the pushed wire and the non-actuated wires of the probe of FIGS. 1A and 2B.

The handle 408 includes a first end region 434, a second end region 436, at least a second portion of the flexor control system 432, a flexor actuator 438, and an interface 440. The first end region 434 is affixed to the second end region 430 of the shaft 410. The second end region 436 represents the other opposing end of the probe 404. The flexor actuator 438 is configured to control the flexor control system 432 to control the flexing of the flexor 426. In one embodiment, the flexor actuator 438 is as shown in FIGS. 1A and 1B. In another embodiment, the flexor actuator 438 includes a ratchet mechanism on each activation wheel. The ratchet mechanism can be switched on/off in the handle 408. In yet another embodiment, the flexor actuator 438 includes an electrical based on/off (and copy) button (electrically) on the handle 408. The interface 440 is configured for connection with a complementary interface of an ultrasound console.

As described in greater detail below, the flexor actuator 438 is configured to mitigate stress induced in the flexor 426 and the flexor control system 432 by actuation of the flexor actuator 438. In one instance, this includes stress induced in the pushed wire for up/down articulation, or stress induced in the pushed wire for left/right articulation. In another instance, this includes stress induced in the non-actuated wires. In yet another instance, this includes both the stress induced in the pushed wire and the stress induced in the non-actuated wires.

It is to be appreciated that the probe 404 can be used for laparoscopic, endoscopic, and/or other applications, and can be used to assist personnel, for example, with an interventional procedure such as a liver, gall bladder, tumor biopsy, etc., guide personnel, for example, with RF ablation, chemical injection, etc. and/or otherwise. As shown, the probe 404 is employed with the console 406. In other embodiments, the probe 404 can be employed with other consoles.

The console 406 includes an interface 442. The interface 442 is complementary to the interface 440 of the probe 404. In one instance, the interface 440 includes a cable with an electro-mechanical connector and the interface 442 includes an electro-mechanical connector. The interfaces 440 and 442 are configured to mechanically engage each other and establish electrical communication there between, e.g., through pins and sockets and/or otherwise. Alternatively, the interfaces 440 and 442 are wireless interfaces.

The console 406 includes a transmit circuit 444 that controls the phasing and/or time of actuation of the individual elements of the transducer array 420, which allows for steering and/or focusing the transmitted beam from predetermined origins along the array and at predetermined angles.

The console 406 further includes a receive circuit 446 that receives signals indicative of the echoes received by the transducer array 420. The receive circuit 446 can beamform (e.g., delays and sums) the echoes into a sequence of focused, coherent echo samples along focused scanlines of a scanplane, and/or otherwise process the echoes.

The console 406 further includes a controller 448 that controls the transmit circuit 444 and/or the receive circuit 446. Such control may include, but is not limited to, controlling the frame rate, number of scan line groups, transmit angles, transmit energies, transmit frequencies, transmit and/or receive delays, etc.

The console 406 further includes a scan converter 450 that scan converts the frames of data to generate data for display, for example, by converting the data to the coordinate system of the display. This may include changing the vertical and/or horizontal scan frequency of signal based on the display. Furthermore, the scan converter 450 can be configured to employ analog and/or digital scan converting techniques.

The console 406 further includes a display 452 that visually presents the rendered data. The display 452 can be integrated in the console 406 or separate therefrom and in electrical communication therewith via a wired and/or wireless connection.

The console 406 further includes a user interface 454 that includes input and/or output devices for interacting with the controller 448 to select a data acquisition mode (e.g., B-mode), initiate scanning, etc. The user interface 454 may include various controls such as buttons, knobs, a keypad, a touch screen, etc. The user interface 454 may also include various types of visual (e.g., LCD, LED, etc.) and/or audible displays.

It is to be understood that the relative size, shape and position of the components of the system 402 are provided for explanatory purposes and are not limiting. In other embodiments, at least one of the size, shape and position of at least one of the components is different.

Figure 5B:
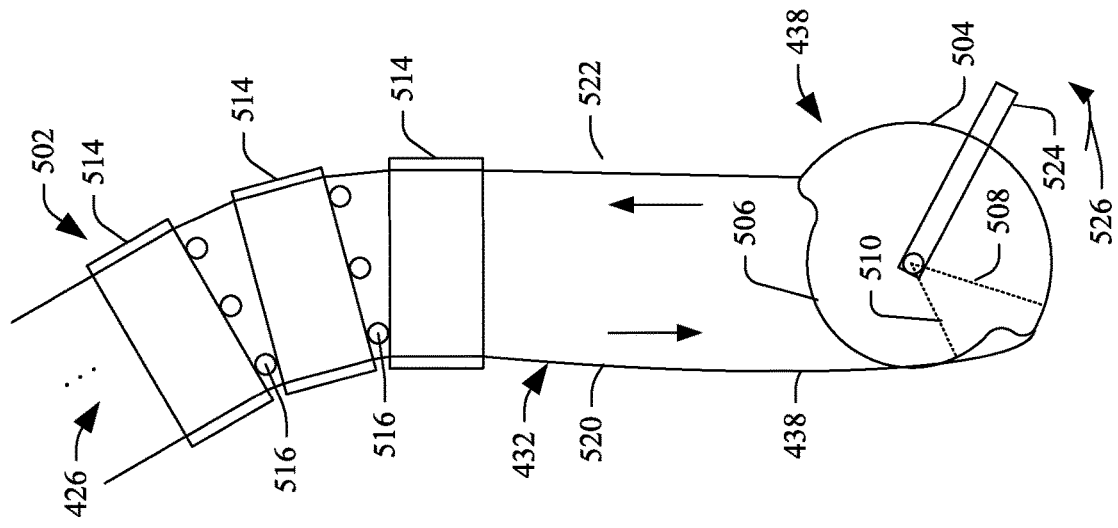
FIG. 5B illustrates the example of the articulation sub-system in use.
Figure 5A:
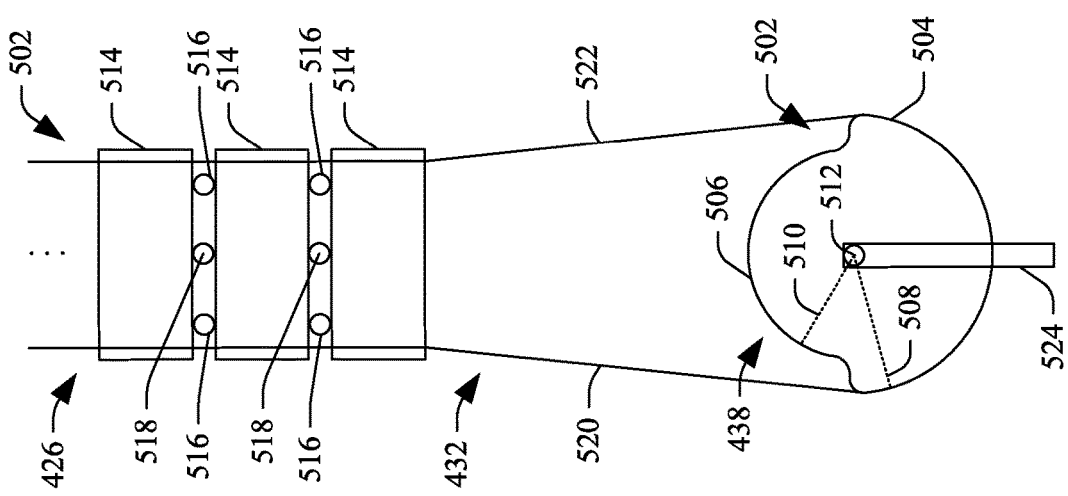
FIG. 5A illustrates an example of the articulation sub-system.

FIG. 5A schematically illustrates an example of the flexor actuator 438, the flexor control system 432, and the flexor 426.

This example is configured to compensate for the difference in the push and pull length of the guides. For sake of clarity and brevity, only one of the up/down or the left/right articulation sub-systems is shown. However, it is to be understood that the up/down or the left/right articulation sub-systems include the same components, with one controlling up/down articulation and the other controlling left/right articulation.

The flexor actuator 438 includes a cam 502. In this example, the cam 502 is disc shaped with two, or first and second half-circles 504 and 506. The first half circle 504 has a first radius 508, and the second half circle 506 has a second radius 510. The first radius 508 is larger than the second radius 510. The cam 502 is rotatably affixed at a rotation axis 512 and is configured to rotate about the rotation axis 512.

The flexor 426 includes a plurality of vertebrae 514. Adjacent pairs of the plurality of vertebrae 514 have two pairs of pivots disposed there between. A first pair of pivots 516 is for left/right (or up/down) articulation. A second pair of pivots 518 (one is behind the other) is for the up/down (or left/right) articulation. The pivots 516 and 518 are all located off-center, with the pivots 518 in a direction transverse or perpendicular to the pivots 516.

The flexor control system 432 includes guides (e.g., wires, strings, cables, or the like) 520 and 522. The guide 520 is connected at a perimeter of one of the ends of the larger half circle 504 at a location where the radius transitions from the larger radius 508 to the smaller radius 510. The guide 522 is connected at a perimeter of the other end of the larger half circle 504, also at a location where the radius transitions from the larger radius 508 to the smaller radius 510. The guides 520 and 522 respectively route through the vertebrae 514, outside of the pivots 516 and 518.

The flexor actuator 438 further includes a lever 524. The lever 524 is stationarily affixed to the cam 502. The lever 524 represents the lever 512 or 514 of FIG. 1. Rotating the lever 512 or 514 rotates the cam 502. Such rotation may include clockwise and/or counter-clockwise rotation.

The plurality of vertebrae 514 are aligned parallel to each other. The cam 502 is oriented so that neither guide 520 or 522 is pulled or pushed. The second half circle 506 faces the plurality of vertebrae 514 and the first half circle 504 faces away from the plurality of vertebrae 514. In this configuration, the articulating member 412 (FIG. 4) and the probe head 414 (FIG. 4) extend straight along the longitudinal axis 415 (FIG. 4), e.g., as shown in FIG. 4, and not articulated.

In FIG. 5B, the lever 524 is rotated in a first or counter-clockwise direction 526. This rotates the cam 502 in the first direction 526. This causes the guide 520 to pull on the plurality of vertebrae 514 on one side of the articulating member 412, and the guide 522 to push on the plurality of vertebrae 514 on the other side of the articulating member 412. In this direction, the plurality of vertebrae 514 pivots on the pivots 516 on the one side, which causes the plurality of vertebrae 514 to separate on the other side.

Figure 5C:
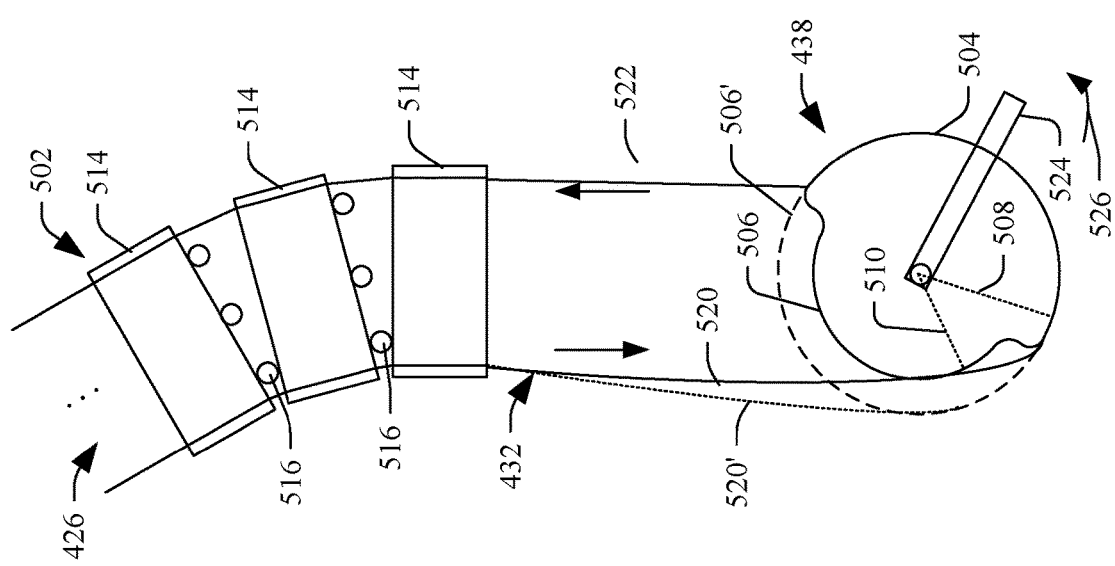
FIG. 5C illustrates the example of the articulation sub-system in connection with prior art.

As shown in FIG. 5C, the smaller radius 510 of the half circle 506 slacks off the pull guide for the same rotational movement, relative to a configuration in which the cam 502 has only the larger radius 508, which is shown in FIG. 5C in connection with a guide 520' and a second half circle 506'. In FIG. 5C, the guide 520' follows a perimeter of the second half circle 506', whereas the guide 520 follows the perimeter of the second half circle 506. This slacking off of the pull guide reduces the stress on the pushed guide. Furthermore, unlike a configuration in which the guides 520 and 522 include springs, the probe head 414 articulates when expected to articulate by the user.

Figure 7:
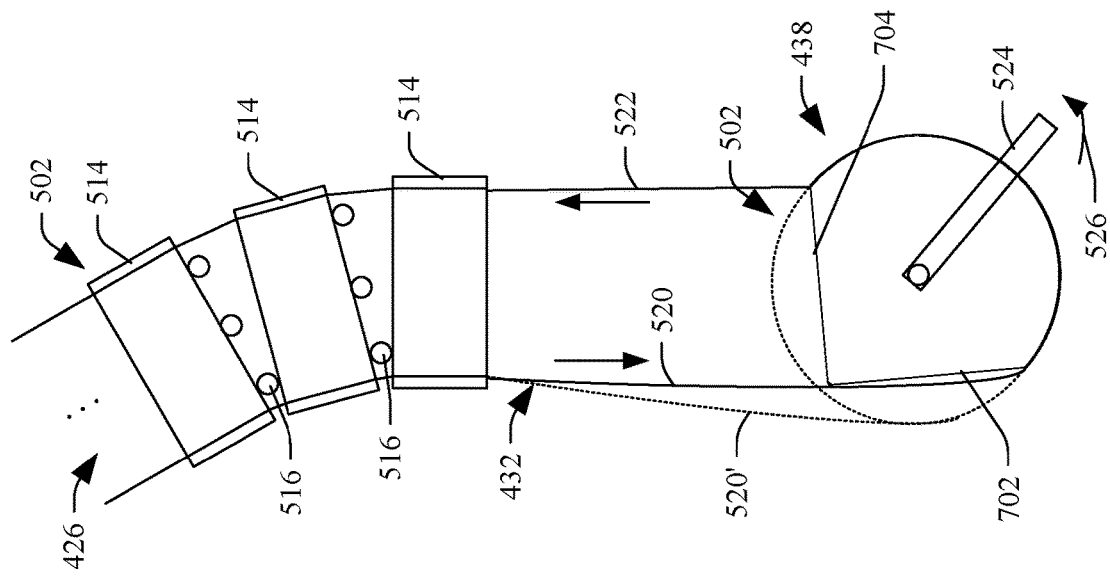
FIG. 7 illustrates a variation of the cam illustrated in FIG. 5.

In general, the cam 502 can have any shape just as long as it provides a guide travel difference between the pull and push sides to reduce the push guide stress. For example, in another embodiment, rather than include the smaller radius 510 with side 506, the cam 502 includes angled sides 702 and 704 as shown in FIG. 7. Other configurations are also included herein.

FIG. 6A schematically illustrates another example of the flexor actuator 438.

This example is configured to compensate for the stress induced in the non-actuated wires. For sake of clarity and brevity, details are shown for only one of the lever/cam/guide sub-systems. However, it is to be understood that both lever/cam/guide sub-systems include the same components and operate the same, with one controlling up/down articulation and the other controlling left/right articulation.

In this example, the flexor actuator 438 for the left/right articulation includes a circular shaped cam 602 with a sub-cam 604. The cam 602 is rotabaly affixed at the rotation axis 512 and is configured to rotate about the rotation axis 512. The flexor 426 for the left/right articulation is substantially similar to that described in FIGS. 5A and 5B and thus will not be described in detail again.

The flexor control system 432 includes a plurality of fixed rotating wheels 606 and a plurality of pivoting rotating wheels 608. The wheels 606 and 608 are all configured to rotate. The wheels 606 are stationarily fixed. The wheels 608 are attached to free ends of pivot members 610, which pivot about pivot points 612. The pivot points 612 are disposed on a translating member 614, which is configured to translate along a rail 616 between the flexor 426 and the cam 524.

The flexor actuator 438 for the up/down articulation includes a similar circular shaped cam 616 with a sub-cam 618. The cam 616 is rotabaly affixed at a rotation axis 620 and is configured to rotate about the rotation axis 620. A lever 622 is attached to the cam 616 and configured to rotate the cam 616. The flexor 426 for the up/down articulation is also substantially similar to that described in FIGS. 5A and 5B and thus will not be described in detail again.

The sub-cam 618 supports a member 624 when the lever 622 is position for no up/down articulation. A translation arm (push) 626 is affixed at one end to the member 624. The member 624 is movable, e.g., on a track which defines a range of movement. When the cam 616 is turned the member 624 moves up the sub-cam 618 and pushes with the translation arm 626 the translating member 614, which causes the pivot members 610 to pivot about the pivot points 612, which will collapse the wheels 608, reducing the stress in the wires 520/522, as described in greater detail next.

In FIG. 6B, the lever 622 is rotated counter-clockwise. This causes down articulation in this example. The member 624 rolls out of the sub-cam 618 and onto the perimeter of the cam 616. As a consequence, the wire 626 moves towards the wheel 628, allowing the translating member 614 to translate towards the articulation member 412. Translation of the translating member 614 results in the pivoting members 610 pivoting towards each other. Such pivoting slacks off the guides 520 and 522 for the left/right articulation.

In one instance, this mitigates the stress induced on the guides 520 and 522 for the left/right articulation due to the down articulation. The same results when rotating in the opposite direction for up articulation. That is, the translating member 614 will translate, slacking off the guides 520 and 522 for the left/right articulation, mitigating the stress induced on the guides 520 and 522 due to the up articulation. When operating the lever 524, the corresponding translating member will translate, slacking off the guides and for the up/down articulation, mitigating the stress induced on these guides due to the left and right articulation.

Another embodiment combines the configurations of FIG. 5A or 7 and 6A. For example, with the combined configurations, the embodiment includes two cams, 506 and 616, with a sub-cam on top of each other, fixed to each other. Other combinations are also contemplated herein.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An elongate ultrasound imaging probe, comprising:
   an articulating member, including:
     at least two vertebrae elements sequentially arranged along a long axis of the elongate ultrasound imaging probe; and
     a plurality of pivots located between the at least two vertebrae elements, wherein each of the plurality of pivots is disposed off-center relative to the at least two vertebrae elements, and each of the plurality of pivots is spatially oriented to provide a pivot point for a different articulation direction of a set of different of articulation directions of a vertebra element of the at least two vertebrae elements;
   a plurality of guides, including at least one guide for each of the respective different pivot directions; and
   a control configured to actuate the plurality of guides for controlling opposing articulation directions.

2. The probe of claim 1, the control, comprising:
   a first control corresponding to first opposing articulation directions, the first control including: a first cam, a first lever and a first guide system, which is configured to control a slack of a pair of guides of the plurality of guides for the first opposing articulation directions; and
   a second control corresponding to second opposing articulation directions, the second control including: a second cam, a second lever, and a member configured to control the first guide system of the first control.

3. The probe of claim 2, wherein the first guide system includes a set of wheels, each attached to a pivoting member, which is pivotably attached to a translating member, which is moveably attached to a slide member.

4. The probe of claim 3, wherein the second cam is circular in shape and includes a sub-cam, and the sub-cam is configured to support the member when the second lever is not actuated, and the member is configured to hold the first guide system at a first position along the slide member.

5. The probe of claim 4, wherein a perimeter of the second cam, excluding the sub-cam, is configured to support the member when the second lever is actuated, and the member is configured to hold the first guide system at a second position along the slide member.

6. The probe of claim 5, wherein the set of wheels is configured to pivot towards each other at the second position.

7. The probe of claim 6, wherein the set of wheels is configured to slack off the pair of guides, thereby reducing stress induced on the non-activated guides.

8. The probe of claim 1, wherein one pair of the guides is configured to control up/down articulation directions and another pair of the guides is configured to control left/right articulation directions.

9. The probe of claim 1, wherein the probe includes a laparoscopic probe.

* * * * *